(12) United States Patent
Akiyama et al.

(10) Patent No.: US 11,969,291 B2
(45) Date of Patent: Apr. 30, 2024

(54) ULTRASONIC DIAGNOSTIC APPARATUS AND ULTRASONIC DIAGNOSTIC METHOD

(71) Applicant: CANON MEDICAL SYSTEMS CORPORATION, Otawara (JP)

(72) Inventors: Mitsuo Akiyama, Otawara (JP); Nobuhide Ooi, Nasushiobara (JP); Koji Ando, Otawara (JP); Kodai Hirayama, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 128 days.

(21) Appl. No.: 16/843,950

(22) Filed: Apr. 9, 2020

(65) Prior Publication Data

US 2020/0330074 A1    Oct. 22, 2020

(30) Foreign Application Priority Data

Apr. 18, 2019  (JP) .................................. 2019-079627
Mar. 30, 2020  (JP) .................................. 2020-059318

(51) Int. Cl.
*A61B 8/00*     (2006.01)
*G06T 7/00*     (2017.01)

(52) U.S. Cl.
CPC ............ *A61B 8/469* (2013.01); *A61B 8/4444* (2013.01); *A61B 8/463* (2013.01); *G06T 7/0012* (2013.01); *G06T 2207/10132* (2013.01); *G06T 2207/30004* (2013.01)

(58) Field of Classification Search
None
See application file for complete search history.

(56) References Cited

U.S. PATENT DOCUMENTS

2010/0036248 A1* 2/2010 Chouno .................. G16H 30/40
                                                             600/443
2016/0206291 A1* 7/2016 Yang ..................... A61B 8/5253
2017/0290569 A1* 10/2017 Utsunomiya .......... A61B 8/466
2019/0392547 A1* 12/2019 Katouzian ............ G06N 3/0445

FOREIGN PATENT DOCUMENTS

| JP | 08-252253 A | 10/1996 |
| JP | 2011-115456 A | 6/2011 |
| JP | 4807824 B2 | 11/2011 |
| JP | 5095186 B2 | 12/2012 |
| JP | 2017-153818 A | 9/2017 |

OTHER PUBLICATIONS

Japanese Office Action issued Aug. 29, 2023, in Japanese Patent Application No. 2020-059318, 3 pages.

* cited by examiner

*Primary Examiner* — Joel Lamprecht
*Assistant Examiner* — Marjan Saboktakin
(74) *Attorney, Agent, or Firm* — Oblon, McClelland, Maier & Neustadt, L.L.P.

(57) ABSTRACT

An ultrasonic diagnostic apparatus according to an embodiment includes a processing circuitry. The processing circuitry is configured to display, as a live image, an image that data output from an ultrasonic probe represents; recognize an image type of the live image; extract, out of past data collected before the live image, data at least a part of which is in common to the image type of the live image; and display an image that the extracted data represents on the same screen as that of the live image.

10 Claims, 6 Drawing Sheets

ULTRASONIC DIAGNOSTIC APPARATUS AND ULTRASONIC DIAGNOSTIC METHOD

CROSS-REFERENCE TO RELATED APPLICATIONS

This application is based upon and claims the benefit of priority from Japanese Patent Application No. 2019-079627, filed on Apr. 18, 2019; and Japanese Patent Application No. 2020-059318, filed on Mar. 30, 2020, the entire contents of which are incorporated herein by reference.

FIELD

Embodiments described herein relate generally to an ultrasonic diagnostic apparatus and an ultrasonic diagnostic method.

BACKGROUND

Conventionally, in an ultrasonic diagnostic apparatus, for example, in the observation after stress echo loading or after treatment such as puncture ablation or the like, displaying a newly obtained ultrasonic image (live image) is performed while referring to an ultrasonic image (reference image) that was obtained before the situation is changed.

For example, conventionally, a technique that matches the brightness of the reference image with that of the live image has been developed. Furthermore, a technique that, by setting an imaging position of the live image on the basis of the display information such as an ROI, a marker, and the like that is set to the reference image, makes the imaging position of the live image identical to that of the reference image has been developed.

However, in the above-described conventional techniques, although it is possible to match the brightness or the imaging position of the reference image with the live image, the identity of image types such as the type of image itself, the type of layout in which the image is displayed, and the like is not taken into consideration, and thus there is room for further improvement in terms of convenience.

DETAILED DESCRIPTION

An ultrasonic diagnostic apparatus according to an embodiment includes a processing circuitry. The processing circuitry is configured to display, as a live image, an image that data output from an ultrasonic probe represents; recognize an image type of the live image; extract, out of past data collected before the live image, data at least a part of which is in common to the image type of the live image; and display an image that the extracted data represents on the same screen as that of the live image.

With reference to the accompanying drawings, exemplary embodiments of an ultrasonic diagnostic apparatus and a computer program will be described.

Figure 1:
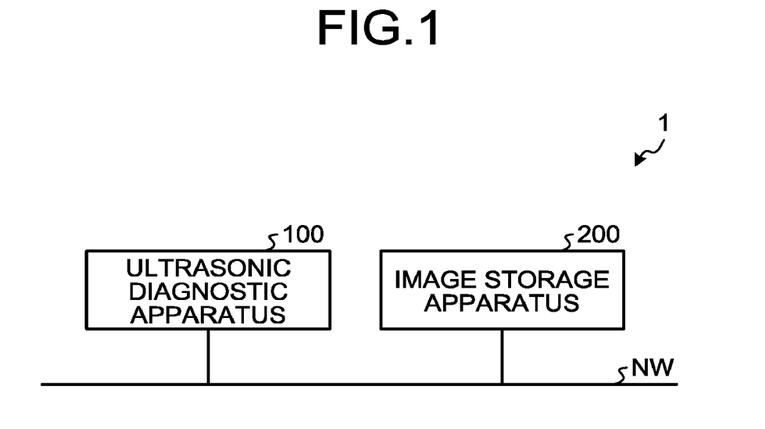
FIG. 1 is a diagram illustrating a configuration example of an ultrasonic diagnostic system according to an embodiment.

FIG. 1 is a diagram illustrating a configuration example of an ultrasonic diagnostic system according to the present embodiment. As illustrated in FIG. 1, an ultrasonic diagnostic system 1 includes an ultrasonic diagnostic apparatus 100 and an image storage apparatus 200. The ultrasonic diagnostic apparatus 100 and the image storage apparatus 200 are in a state capable of performing communication with each other via a network NW such as an in-hospital local area network (LAN) installed in a hospital, for example. If, for example, a picture archiving and communication system (PACS) is adopted in the ultrasonic diagnostic system 1, each device mutually transmits and receives medical data and the like in accordance with the digital imaging and communications in medicine (DICOM) standard.

The ultrasonic diagnostic apparatus 100 acquires, by transmitting ultrasound to the body by using an ultrasonic probe, data that can represent an ultrasonic image of any desired cross-section. The ultrasonic diagnostic apparatus 100 then transmits the acquired data to the image storage apparatus 200.

The image storage apparatus 200 is a database that stores therein medical data. The image storage apparatus 200 stores the data transmitted from the ultrasonic diagnostic apparatus 100 in storage. The storage is implemented by a semiconductor memory device such as a random access memory (RAM), a flash memory, and the like, a hard disk, or an optical disk, for example.

In this case, the data stored in the image storage apparatus 200 may be RAW data which will be described later or may be ultrasonic images generated from the relevant RAW data. In addition, the data is stored in association with supplementary information including a subject ID that is an identifier (ID) of a subject, an examination ID that is an ID of an examination performed on the subject, a device ID that is an ID of a device used in the examination, an image type which will be described later, and the like.

Figure 2:
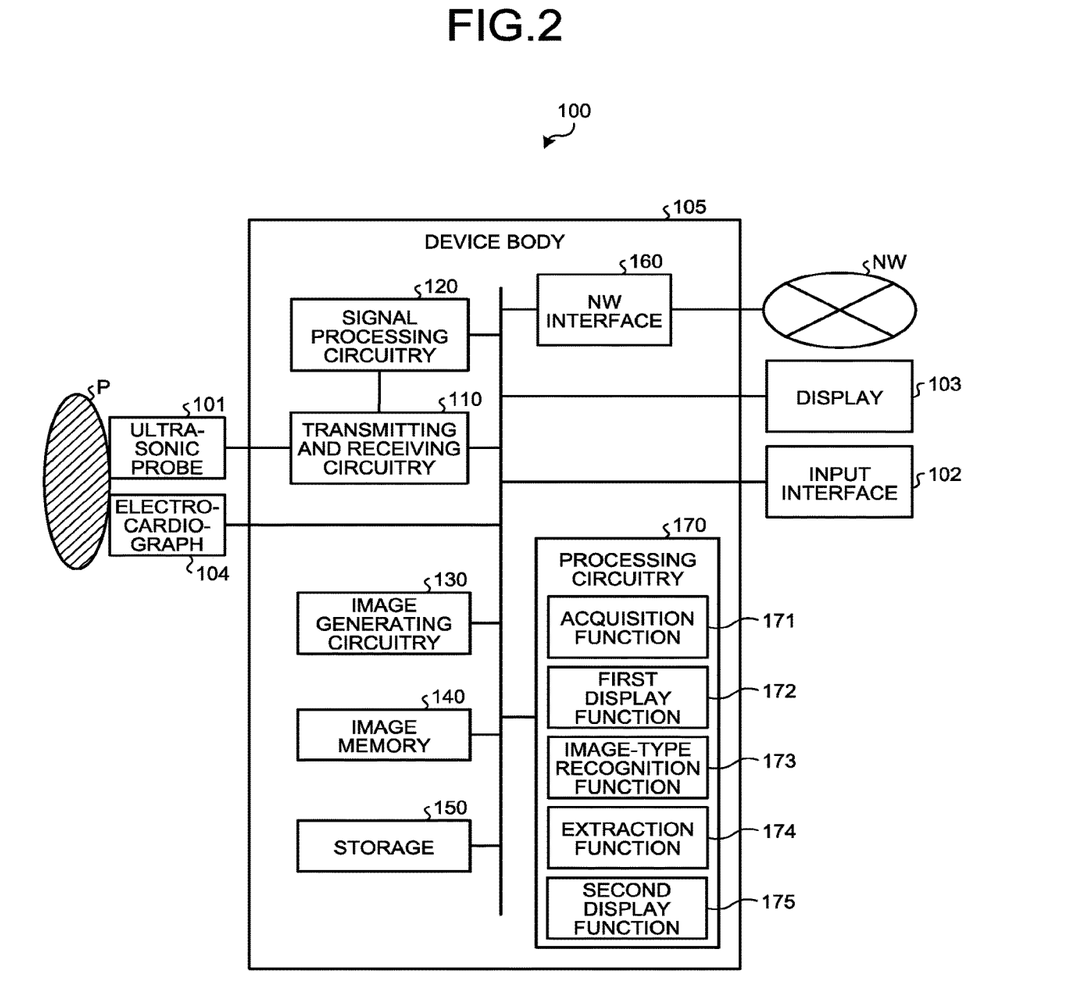
FIG. 2 is a block diagram illustrating a configuration example of an ultrasonic diagnostic apparatus in the embodiment.

FIG. 2 is a block diagram illustrating a configuration example of the ultrasonic diagnostic apparatus 100. As illustrated in FIG. 2, the ultrasonic diagnostic apparatus 100 includes an ultrasonic probe 101, an input interface 102, a display 103, an electrocardiograph 104, and a device body 105. The ultrasonic probe 101, the input interface 102, the display 103, and the electrocardiograph 104 are connected to the device body 105 so as to be capable of performing communication.

The ultrasonic probe 101 includes a plurality of transducer elements, and these transducer elements generate ultrasound on the basis of drive signals supplied from a transmitting and receiving circuitry 110 that the device body 105 includes. The ultrasonic probe 101 further receives reflected waves from a subject P and converts them into electrical signals. The ultrasonic probe 101 is detachably connected to the device body 105.

When the ultrasound is transmitted to the subject P from the ultrasonic probe 101, the transmitted ultrasound is reflected one after another on discontinuous surfaces of acoustic impedance in the body tissue of the subject P and is received by the multiple transducer elements of the ultrasonic probe 101 as reflected wave signals. The amplitude of the received reflected wave signals depends on the difference in acoustic impedance of the discontinuous surfaces on which the ultrasound is reflected. The reflected wave signal when the transmitted ultrasonic pulses are reflected on moving blood flow or a surface such as a cardiac wall and the like is, due to the Doppler effect, subjected to frequency deviation dependent on the velocity component of a moving body with respect to the ultrasound transmission direction.

The mode of the ultrasonic probe 101 does not matter in particular, and an ultrasonic probe of any mode may be used. For example, the ultrasonic probe 101 may be a 1D array probe that scans the subject P in two dimensions. The ultrasonic probe 101 may be a mechanical 4D probe or a 2D array probe that scans the subject P in three dimensions.

The input interface 102 receives the input operation of a variety of instructions and information from an operator. Specifically, the input interface 102 converts the input operation received from the operator into an electrical signal and outputs it to a processing circuitry 170 of the device body 105. For example, the input interface 102 is implemented by a trackball, switch buttons, a mouse, a keyboard, a touchpad that performs input operation by touching an operating surface, a touch screen in which a display screen and a touchpad are integrated with, a non-contact input circuitry using an optical sensor, an audio input circuitry, and the like. The input interface 102 is not limited to those having a physical operating component such as a mouse, a keyboard, and the like. Examples of the input interface 102 further include an electrical-signal processing circuitry that receives an electrical signal corresponding to the input operation from an external input device provided separately from the device and outputs this electrical signal to a control circuitry.

The display 103 displays a variety of information and images. Specifically, the display 103 converts and outputs data of information and images sent from the processing circuitry 170 into an electrical signal for display. For example, the display 103 is implemented with a liquid crystal monitor, a cathode ray tube (CRT) monitor, a touch panel, and the like. As the output device that the ultrasonic diagnostic apparatus 100 includes, it is not limited to the display 103, and a speaker may be included, for example. The speaker outputs a predetermined sound such as a beep sound in order to inform the operator of the processing status of the device body 105, for example.

The electrocardiograph 104 acquires, as a biosignal of the subject P, the electrocardiogram (ECG) of the subject P. The electrocardiograph 104 transmits the acquired electrocardiogram to the device body 105.

The device body 105 is a device that generates ultrasonic images on the basis of the reflected wave signals received by the ultrasonic probe 101. For example, the device body 105 generates two-dimensional ultrasonic images on the basis of the two-dimensional reflected wave data received by the ultrasonic probe 101. In addition, the device body 105 generates three-dimensional ultrasonic images on the basis of the three-dimensional reflected wave data received by the ultrasonic probe 101.

The device body 105 includes, as illustrated in FIG. 2, the transmitting and receiving circuitry 110, a signal processing circuitry 120, an image generating circuitry 130, an image memory 140, a storage 150, a network (NW) interface 160, and the processing circuitry 170. The transmitting and receiving circuitry 110, the signal processing circuitry 120, the image generating circuitry 130, the image memory 140, the storage 150, the NW interface 160, and the processing circuitry 170 are connected so as to be capable of performing communication with one another.

The transmitting and receiving circuitry 110 includes a pulse generator, a transmission delay unit, a pulser, and the like and supplies drive signals to the ultrasonic probe 101. The pulse generator repeatedly generates, at a predetermined rate frequency, rate pulses for forming the transmitting ultrasound. The transmission delay unit gives, to each rate pulse generated by the pulse generator, a delay time needed for each transducer element to focus the ultrasound generated from the ultrasonic probe 101 in a beam-like form and to determine the transmission directivity. The pulser applies, at the timing based on the rate pulse, the drive signals (drive pulses) to the ultrasonic probe 101. That is, the transmission delay unit arbitrarily adjusts, by varying the delay time given to each rate pulse, the transmission direction of the ultrasound transmitted from the transducer element plane.

The transmitting and receiving circuitry 110 includes a preamplifier, an A/D (analog/digital) converter, a receiving delay unit, an adder, and the like and, by performing various processing on the reflected wave signals received by the ultrasonic probe 101, generates reflected wave data. The preamplifier amplifies the reflected wave signal for each channel. The A/D converter performs A/D conversion on the amplified reflected wave signals. The receiving delay unit gives a delay time needed to determine the receiving directivity. The adder generates, by addition processing of the reflected wave signals processed by the receiving delay unit, the reflected wave data. Due to the addition processing of the adder, the reflected component from the direction corresponding to the receiving directivity of the reflected wave signals is emphasized and, by the receiving directivity and the transmission directivity, an overall beam of the ultrasound transmitting and receiving is formed.

The form of the output signal from the transmitting and receiving circuitry 110 is selectable from various forms, such as a signal that contains phase information referred to as a radio frequency (RF) signal, amplitude information after envelope detection processing, and the like.

The signal processing circuitry 120 receives the reflected wave data from the transmitting and receiving circuitry 110, performs logarithmic amplification, envelope detection processing, and the like, and generates data (B-mode data) for which the signal strength is represented in brightness. The signal processing circuitry 120 further performs frequency analysis on the velocity information from the reflected wave data received from the transmitting and receiving circuitry 110, extracts blood flow, tissue, and contrast echo components, and generates data (Doppler data) for which moving body information such as the velocity, dispersion, power, and the like is extracted from multiple points.

In addition, the signal processing circuitry 120 is capable of processing both two-dimensional reflected wave data and three-dimensional reflected wave data. That is, the signal processing circuitry 120 generates two-dimensional B-mode data from the two-dimensional reflected wave data and generates three-dimensional B-mode data from the three-dimensional reflected wave data. The signal processing circuitry 120 further generates two-dimensional Doppler data from the two-dimensional reflected wave data and generates three-dimensional Doppler data from the three-dimensional reflected wave data.

The image generating circuitry 130 generates ultrasonic images from the data generated by the signal processing circuitry 120. For example, the image generating circuitry 130 generates two-dimensional B-mode images representing the strength of the reflected waves in brightness from the two-dimensional B-mode data generated by the signal processing circuitry 120.

For example, the image generating circuitry 130 generates two-dimensional Doppler images in which blood flow information is visualized, from the two-dimensional Doppler data generated by the signal processing circuitry 120. The two-dimensional Doppler image is velocity image data representing the average velocity of blood flow, dispersion image data representing a dispersion value of the blood flow, power image data representing the power of the blood flow, or image data that the foregoing are combined. In addition, the image generating circuitry 130 generates, as the Doppler images, color Doppler images in which blood flow information such as the average velocity, dispersion value, power, and the like of the blood flow is displayed in color or generates the Doppler images in which a single piece of blood flow information is displayed in grayscale.

Furthermore, for example, the image generating circuitry 130 can also generate M-mode images from the time series data of the B-mode data on a single scanning line generated by the signal processing circuitry 120. The image generating circuitry 130 can also generate Doppler waveforms for which the velocity information on blood flow and tissue is plotted along the time series, from the Doppler data generated by the signal processing circuitry 120.

The image generating circuitry 130, in general, converts the stream of scanning line signals of ultrasonic scanning into the stream of scanning line signals of video format represented by television and the like (scan conversion) and generates ultrasonic images for display. Specifically, the image generating circuitry 130 performs coordinate conversion according to the scanning mode of ultrasound by the ultrasonic probe 101, thereby generating ultrasonic images for display. The image generating circuitry 130 performs, as various image processing in addition to the scan conversion, by using a plurality of image frames after scan conversion, the image processing of regenerating average brightness images (smoothing processing), the image processing that uses differential filters in the image (edge enhancement processing), and the like, for example. In addition, the image generating circuitry 130 combines character information, scales, body marks, and the like of various parameters to the ultrasonic image data.

That is, the B-mode data and the Doppler data are data before scan conversion processing, and the data generated by the image generating circuitry 130 is the image data for display after scan conversion processing. In the following description, the data before scan conversion processing (B-mode data and Doppler data) may also be referred to as "RAW data".

The image generating circuitry 130 generates, from the two-dimensional B-mode data and the two-dimensional Doppler data that are RAW data, the two-dimensional B-mode images and two-dimensional Doppler images that are two-dimensional ultrasonic images. The image generating circuitry 130 can further generate a superimposed image for which a color Doppler image is superimposed on a two-dimensional B-mode image, for example.

The image memory 140 is one example of storage. The image memory 140 is a memory that stores therein ultrasonic images generated by the image generating circuitry 130. The image memory 140 can also store therein the RAW data generated by the signal processing circuitry 120. The RAW data stored in the image memory 140 can be recalled by the operator after diagnosis and, by going through the image generating circuitry 130, can be displayed as the ultrasonic image. The image generating circuitry 130 further stores, in the image memory 140, the ultrasonic image and the time of ultrasonic scanning (scanning) performed to generate the relevant ultrasonic image, in association with the electrocardiogram transmitted from the electrocardiograph 104.

The storage 150 stores therein various data. For example, the storage 150 stores therein control programs for performing ultrasound transmitting and receiving, image processing, and display processing, and various data such as diagnostic information (for example, patient's ID, findings of physicians, and the like), diagnostic protocols, various body marks, and the like. In addition, the storage 150 is also used, as needed, for the storage of ultrasonic images and RAW data that the image memory 140 stores. For example, the storage 150 is implemented with a semiconductor memory device such as a random access memory (RAM), a flash memory, and the like, a hard disk drive (HDD), an optical disk, or the like.

The data stored by the storage 150 can be transferred to an external device via the NW interface 160. Examples of the external device include a personal computer (PC) or a tablet device that is used by a physician who performs image diagnosis, the image storage apparatus 200 that stores therein images, a printer, and the like.

The NW interface 160 controls the communication performed between the device body 105 and an external device. Specifically, the NW interface 160 receives various information from the external device and outputs the received information to the processing circuitry 170. For example, the NW interface 160 is implemented with a network card, a network adapter, a network interface controller (NIC), and the like.

In the present embodiment, although the case in which the ultrasonic diagnostic apparatus 100 is connected to an external device (the image storage apparatus 200 and the like) so as to be capable of performing communication via the network NW will be described, the embodiments are not limited thereto. For example, the ultrasonic diagnostic apparatus 100 is capable of exchanging information with an external device via a storage medium, a detachable storage (an external HDD device and the like), or the like, without going through the network NW.

The processing circuitry 170 controls the entire processing of the ultrasonic diagnostic apparatus 100. Specifically, the processing circuitry 170 controls, on the basis of various setting requests input from the operator via the input interface 102, and various control programs and various data read out from the storage 150, the processing of the transmitting and receiving circuitry 110, the signal processing circuitry 120, and the image generating circuitry 130. The processing circuitry 170 further controls the display of the ultrasonic image.

In addition, the processing circuitry 170 executes an acquisition function 171, a first display function 172, an image-type recognition function 173, an extraction function 174, and a second display function 175. In this case, the acquisition function 171 is one example of an acquisition unit. The first display function 172 is one example of a first display unit. The image-type recognition function 173 is one example of an image-type recognition unit. The extraction function 174 is one example of an extraction unit. The second display function 175 is one example of a second display unit.

For example, various processing functions executed by the acquisition function 171, the first display function 172, the image-type recognition function 173, the extraction function 174, and the second display function 175 that are the constituent elements of the processing circuitry 170 illustrated in FIG. 1 are recorded in the storage 150 in a form of computer programs executable by a computer. The processing circuitry 170 is a processor that, by reading out and executing each program from the storage 150, implements the functions corresponding to the respective programs. In other words, the processing circuitry 170 in a state of having read out the respective programs has the respective functions that are indicated in the processing circuitry 170 illustrated in FIG. 2.

In the present embodiment, although it is described that each of the following processing functions is implemented in a single processing circuitry 170, it does not matter even if the processing circuitry is configured with a plurality of independent processors in combination and the respective processors implement each function by executing the programs.

The acquisition function 171 acquires data output from the ultrasonic probe 101. For example, the ultrasonic diagnostic apparatus 100 collects reflected wave data by performing ultrasonic scanning on a specific region of the subject P. The ultrasonic diagnostic apparatus 100 (the image generating circuitry 130) generates, based on the collected reflected wave data, a plurality of ultrasonic images (ultrasonic image group) for display arranged in time series. The generated ultrasonic images are stored in the image memory 140 for the purpose of display. The acquisition function 171 reads out the ultrasonic images stored in the image memory 140 in chronological order.

The first display function 172 displays on the display 103 the ultrasonic images acquired by the acquisition function 171 as a real-time live image. Specifically, the first display function 172 displays, based on a predetermined display layout, the live image on the display 103.

In this case, the display layout is a layout for which the layout of the ultrasonic image that is the subject of display on the screen is defined, and is stored in the storage 150 and the like in advance as setting information. The display layout is prepared for each type of ultrasonic diagnosis or for each type of ultrasonic image generated by the image generating circuitry 130.

The display layout used for the display of live image may be determined automatically depending on the operation via the input interface 102, or the type of ultrasonic image generated by the image generating circuitry 130 or may be determined by the first display function 172.

Figure 3:
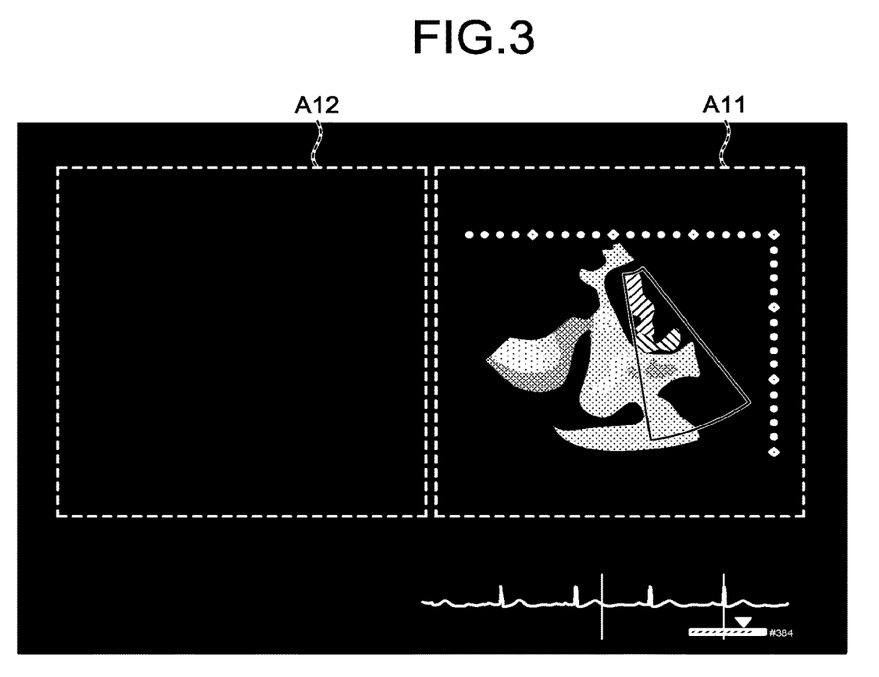
FIG. 3 is a diagram illustrating one example of a live image displayed by a first display function of the embodiment.

FIG. 3 is a diagram illustrating one example of the live image displayed by the first display function 172. The display screen illustrated in FIG. 3 has two display areas A11 and A12 as the display layout. In this case, for example, assuming that the display area A11 at the right of the screen is the display area for displaying the live image and the display area A12 at the left of the screen is the display area for displaying reference image which will be described later, the first display function 172 displays the live image generated by the image generating circuitry 130 in the display area A11.

In FIG. 3, illustrated is an example in which a superimposed image of a color Doppler image superimposed on the two-dimensional B-mode image is displayed in the display area A11 as the live image. In addition, below the display area A11, the electrocardiogram obtained by the electrocardiograph 104 is displayed.

Figure 4:
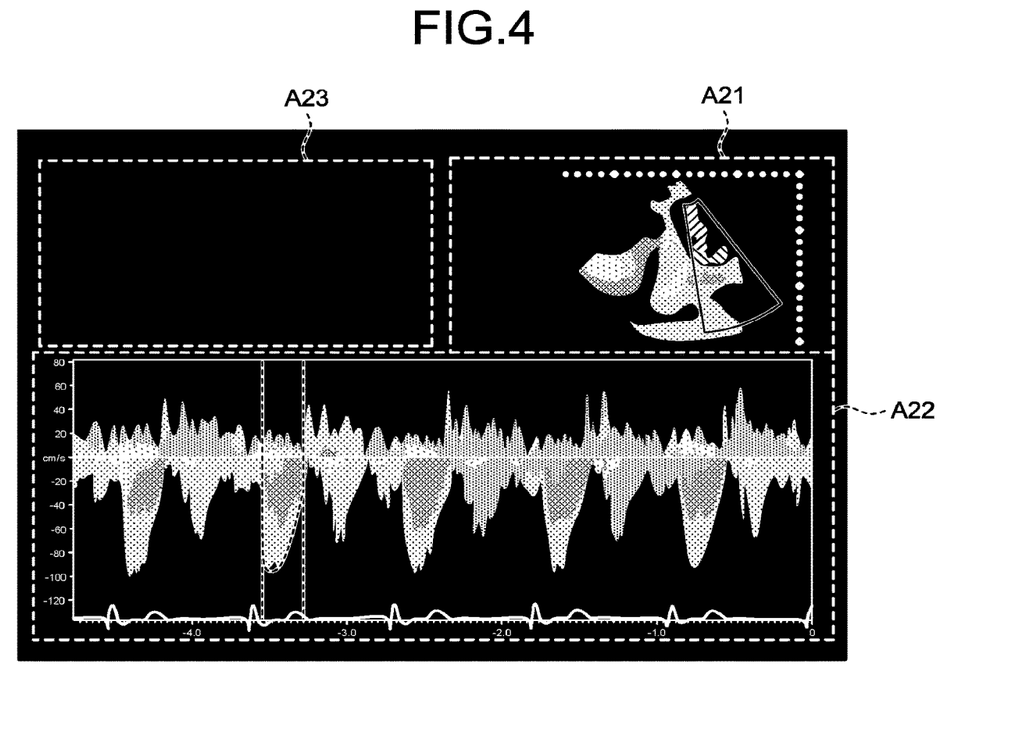
FIG. 4 is a diagram illustrating one example of a live image displayed by the first display function of the embodiment.

FIG. 4 is a diagram illustrating one example of the live image displayed by the first display function 172. The display screen illustrated in FIG. 4 has, as the display layout, three display areas A21, A22, and A23. In this case, for example, assuming that the display area A21 at the upper right of the screen and the display area A22 in the lower screen are the display areas for displaying the live images and the display area A23 at the upper left of the screen is the display area for displaying the reference image described later, the first display function 172 displays the live images generated by the image generating circuitry 130 in the display area A21 and the display area A22.

In FIG. 4, illustrated is an example of a triplet display in which the live image (superimposed image) the same as that of FIG. 3 is displayed in the display area A21 and a two-dimensional pulse-Doppler image is displayed in the display area A22 as the live image. In addition, below the display area A22, the electrocardiogram obtained by the electrocardiograph 104 is displayed.

The display layout is not limited to the examples of FIG. 3 and FIG. 4. It is also possible to arbitrarily set the type of live image displayed in each area.

Referring back to FIG. 2, the image-type recognition function 173 recognizes the image type of the live image displayed by the first display function 172. In this case, the image type is a concept that includes, regardless of the type of live image itself, the type concerning the display of the relevant live image.

Specifically, the image-type recognition function 173, by collaborating with the signal processing circuitry 120, the image generating circuitry 130, and the like, recognizes, as the image type, the mode type (for example, B-mode, M-mode, color Doppler, pulse Doppler, and the like) of the live image.

Furthermore, the image-type recognition function 173, by collaborating with the signal processing circuitry 120, the image generating circuitry 130, and the like, recognizes, as the image type, the dimensionality (for example, two-dimension, three-dimension, and the like) of the ultrasonic image represented as the live image. The image-type recognition function 173, by collaborating with the first display function 172 and the like, further recognizes, as the image type, the type of display layout concerning the display of the live image. In addition, when the subject of scanning is the heart, the image-type recognition function 173, by recognizing the shape of a structure represented in the live image, recognizes, as the image type, the cross-section type (for example, a short-axis view, a 4-chamber view, and the like) of the cross-section of the subject.

For example, in the case of the live image illustrated in FIG. 3, the image-type recognition function 173 recognizes that, as the image type of the relevant live image, it is a two-dimensional B-mode image, a two-dimensional color Doppler image, a superimposed image for which the foregoing images are superimposed, and the like. The image-type recognition function 173 further recognizes, as the image type of the live image, the display layout that singly displays the superimposed image and the like.

For example, in the case of the live image illustrated in FIG. 4, the image-type recognition function 173 recognizes that, as the image type of the relevant live image, it is a two-dimensional B-mode image, a two-dimensional color Doppler image, a two-dimensional pulse-Doppler image, and the like. The image-type recognition function 173 further recognizes, as the image type of the live image, the display layout in which the superimposed image of the B-mode image and the color Doppler image, and the pulse-Doppler image are vertically arranged and the like.

The extraction function 174 extracts, based on the image types of the live image recognized by the image-type recognition function 173, ultrasonic data having at least a part of the relevant image types from the image storage apparatus 200.

Specifically, the extraction function 174 narrows down, out of the data stored in the image storage apparatus 200 in association with the subject ID of the subject P to be the subject of scanning (hereinafter also referred to as past data), the past data for which the same scanning region as the live image has been imaged. Then, the extraction function 174 extracts, out of the condition of image types recognized by the image-type recognition function 173, the past data that satisfies at least a part of the condition from the narrowed down past data. It is assumed that the past data of the subject of extraction is not limited to the ultrasonic images and includes the PAW data. For example, when the image type of the live image is a two-dimensional B-mode image, the extraction function 174 extracts two-dimensional B-mode data as the RAW data that satisfies the condition of the relevant image type.

The image type of the past data can be determined by the following methods, for example. Specifically, the extraction function 174 determines, based on the information included in the supplementary information (for example, the view mode and the like that is stored in the DICOM tag information), a scanning mode, dimensionality, a cross-section type, and the like. The extraction function 174, when the past data is the ultrasonic image, further determines the type of display layout from the content of the ultrasonic image.

Out of a plurality of image types, a condition setting of which image type to set as a prerequisite can be set arbitrarily. For example, out of the mode type, the dimensionality, the display layout, and the cross-section type, the fact that the mode type and the dimensionality match those of the live image may be set as a prerequisite. Such a condition setting is stored in the storage 150 as the setting information, for example.

The timing that the extraction function 174 starts extracting the ultrasonic data does not matter in particular, and the extraction can be started at any desired timing. For example, when directed to perform stress echo examination, the extraction function 174 may, at the time of scanning after stress (motion or dobutamine) loading, start extracting from the data acquired before the stress loading. Furthermore, for example, at the time of scanning after treatment such as puncture ablation or the like is performed, the extraction function 174 may start extracting from the data acquired before the treatment.

The second display function 175 displays as the reference image the ultrasonic image based on the past data extracted by the extraction function 174 on the same screen as that of the live image. Specifically, the second display function 175 displays the reference image within the display layout in which the live image is displayed. In this case, the second display function 175 switches the display methods of the reference image in accordance with whether the past data extracted by the extraction function 174 is the ultrasonic image or the RAW data.

For example, when the extracted past data is the ultrasonic image of the same image type as that of the live image, the second display function 175 displays, as the reference image, the ultrasonic image as is. In this case, the reference image displayed represents the same image type as that of the live image. Furthermore, for example, when the extracted past data is the ultrasonic image that satisfies only a part of the condition of image types of the live image, the second display function 175 displays, as the reference image, the ultrasonic image as is.

In addition, for example, when the extracted past data is the RAW data, the second display function 175 generates from the relevant RAW data, by collaborating with the image generating circuitry 130 and the like, the ultrasonic image of the same image type as that of the live image. Then, the second display function 175 displays on the display 103 the ultrasonic image generated from the RAW data as the reference image. As one example, when the live image is a superimposed image of a two-dimensional B-mode image and a color Doppler image, from the two-dimensional B-mode data and the Doppler data extracted as the RAW data, a superimposed image the same as that of the live image can be generated.

Figure 5:
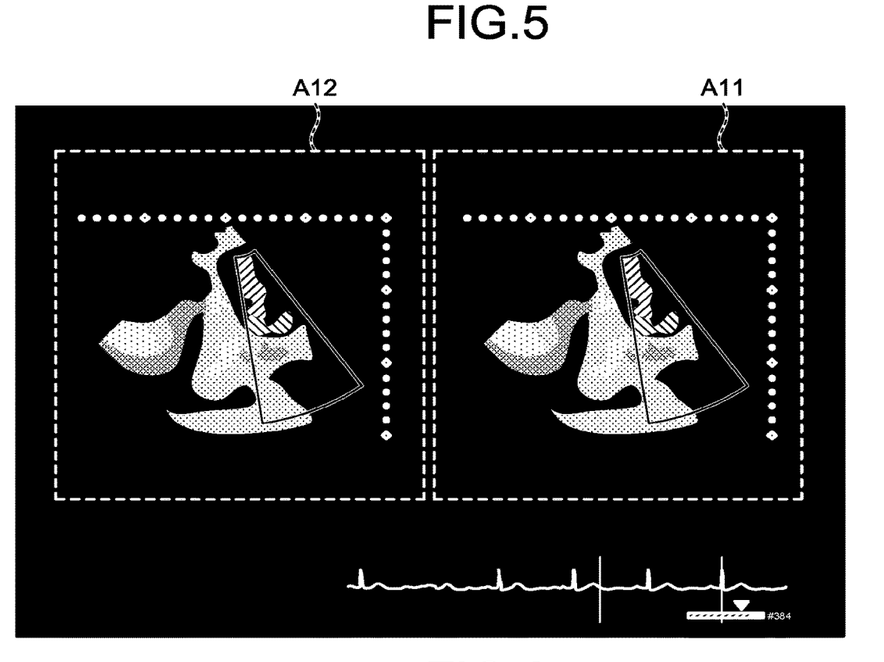
FIG. 5 is a diagram illustrating one example of a reference image displayed by a second display function of the embodiment.
Figure 6:
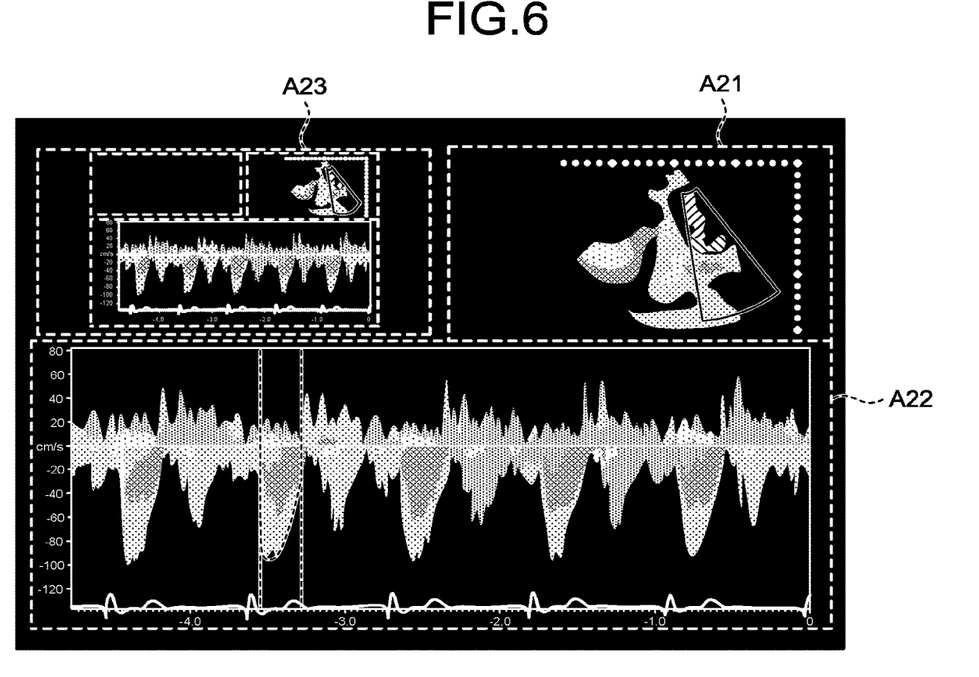
FIG. 6 is a diagram illustrating one example of a reference image displayed by the second display function of the embodiment.
Figure 7:
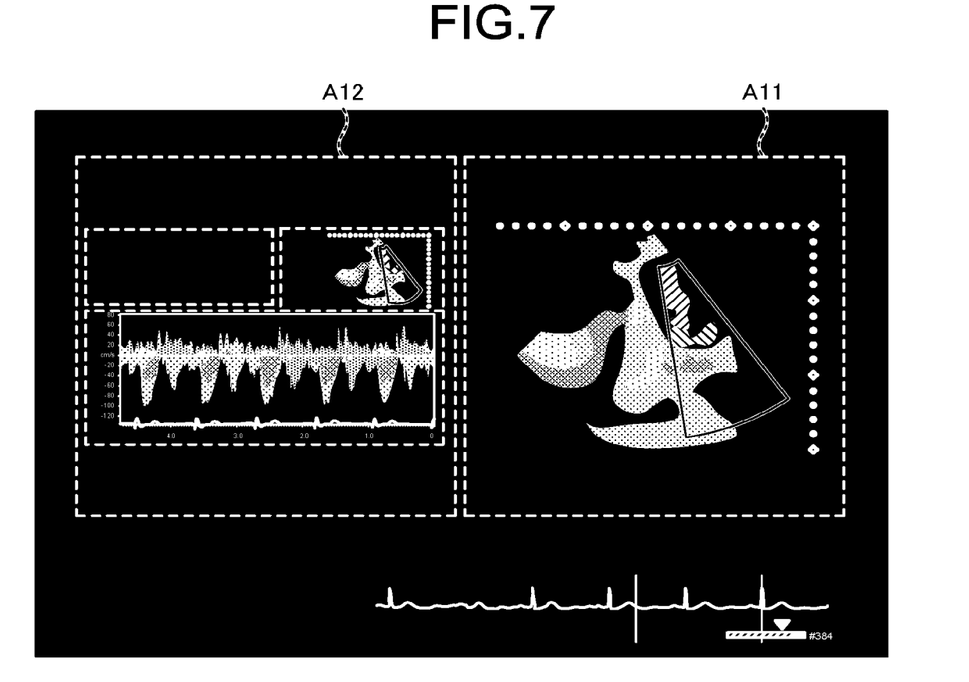
FIG. 7 is a diagram illustrating one example of a reference image displayed by the second display function of the embodiment.

FIG. 5 to FIG. 7 are diagrams illustrating one example of the reference image displayed by the second display function 175. FIG. 5 and FIG. 7 correspond to the display screen of FIG. 3, and FIG. 6 corresponds to the display screen of FIG. 4.

For example, when the ultrasonic image of the same image type as that of the live image illustrated in FIG. 3 is extracted as the past data, as illustrated in FIG. 5, the second display function 175 displays, as the reference image, the extracted ultrasonic image in the display area A12. In this case, the reference image displayed represents the same image type as that of the live image.

Furthermore, for example, when the RAW data a part of image types (mode type) of which is in common to the live image illustrated in FIG. 4 is extracted as the past data, as illustrated in FIG. 6, the second display function 175 displays, as the reference image, the ultrasonic image of the same image type as that of the live image generated from the extracted RAW data in the third display area A23. In this case, the reference image displayed represents the same image type as that of the live image.

In addition, for example, when the ultrasonic image for which a part of image types (mode type) is in common to the live image illustrated in FIG. 3 is extracted as the past data, as illustrated in FIG. 7, the second display function 175 displays, as the reference image, the extracted past data as is in the display area A12. In this case, the reference image displayed is different in a part of the image types from the live image.

As in the foregoing, the ultrasonic diagnostic apparatus 100 displays, together with the live image, the reference image for which a part of or the whole of image types is in common to the image type of the relevant live image. As a result, because the ultrasonic diagnostic apparatus 100 can display the reference image corresponding to the image type of the live image, the ease of comparison between the live image and the reference image can be improved. In the display modes described in FIG. 5 and FIG. 6, because the live image and the reference image can be displayed in the same display layout, the position at which the ultrasonic image of the same type is displayed can be understood intuitively from the positional relation of the display layout and the improvement of convenience can be achieved.

In the above-described examples, the examples in which the second display function 175 displays the reference image after the live image is displayed by the first display function 172 have been described, but the order of display is not limited thereto. For example, when the image type of the live image can be obtained before the relevant live image is displayed, the reference image may be displayed ahead of the display of the live image.

Next, with reference to FIG. 8 and FIG. 9, operation examples of the above-described ultrasonic diagnostic apparatus 100 will be described. In the following description, the operation of the ultrasonic diagnostic apparatus 100 is described separating into two parts of the first operation and the second operation. The first operation corresponds to the operation in collecting in-vivo images of the subject P, for example, before stress loading or before performing treatment such as puncture ablation or the like. The second operation corresponds to the operation in collecting in-vivo images of the subject P in the observation, for example, performed after stress loading or after treatment such as puncture ablation or the like.

Figure 8:
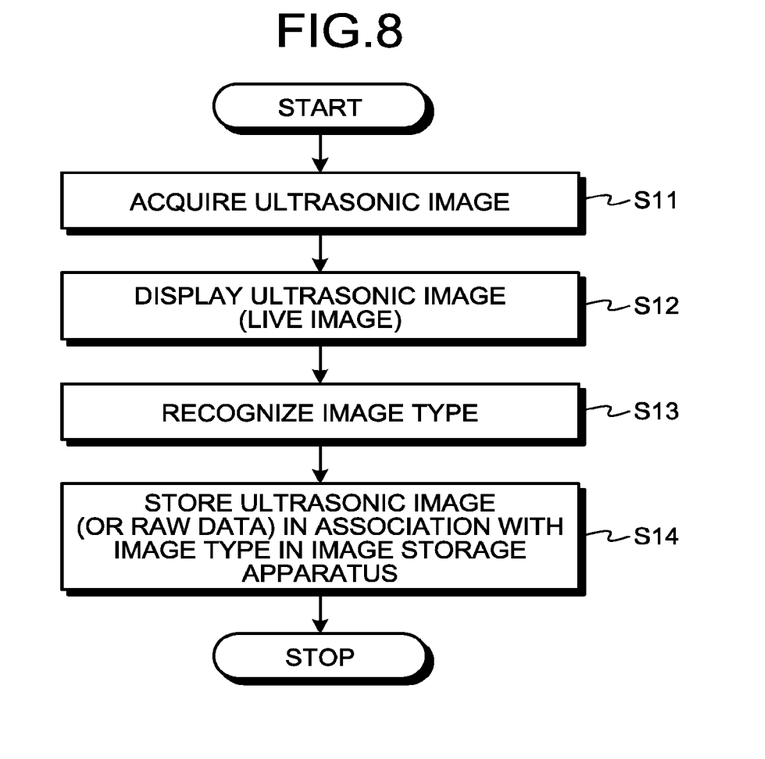
FIG. 8 is a flowchart illustrating one example of a first operation performed by the ultrasonic diagnostic apparatus of the embodiment.

FIG. 8 is a flowchart illustrating one example of the first operation performed by the ultrasonic diagnostic apparatus 100. First, when imaging of the subject P is performed by using the ultrasonic probe 101, the image generating circuitry 130 generates an ultrasonic image on the basis of the data output from the ultrasonic probe 101.

The acquisition function 171 acquires the ultrasonic image generated by the image generating circuitry 130 (Step S11). Then, the first display function 172 displays on the display 103 the ultrasonic image acquired by the acquisition function 171 as the live image (Step S12). Furthermore, the image-type recognition function 173 recognizes the image type of the displayed live image (Step S13).

Then, when storing the ultrasonic image, or the RAW data relating to generating the relevant ultrasonic image, the processing circuitry 170 stores in the image storage apparatus 200 the ultrasonic image or the RAW data collected in the imaging of this time in association with the information indicating the image type recognized at Step S13 (Step S14).

In this case, the image type to be the subject of storing does not matter in particular, and it may be stored including the display layout, in addition to the image types that directly relate to the imaging of the subject P (mode type, dimensionality, cross-section type). Storing the collected diagnostic result data in association with the image type of the diagnostic result data thereof allows the processing to be performed efficiently in extracting the reference data from the image storage apparatus 200.

In addition, it is assumed that the processing circuitry 170 also stores, in association with the reference image, the information representing the subject ID of the subject P, the examination ID, the device ID, and an imaging target region. It is further assumed that, when the image type is changed during the first operation, for example when the change of scanning mode or the change of display layout is performed, the reference images before and after the change are stored as separate data.

Figure 9:
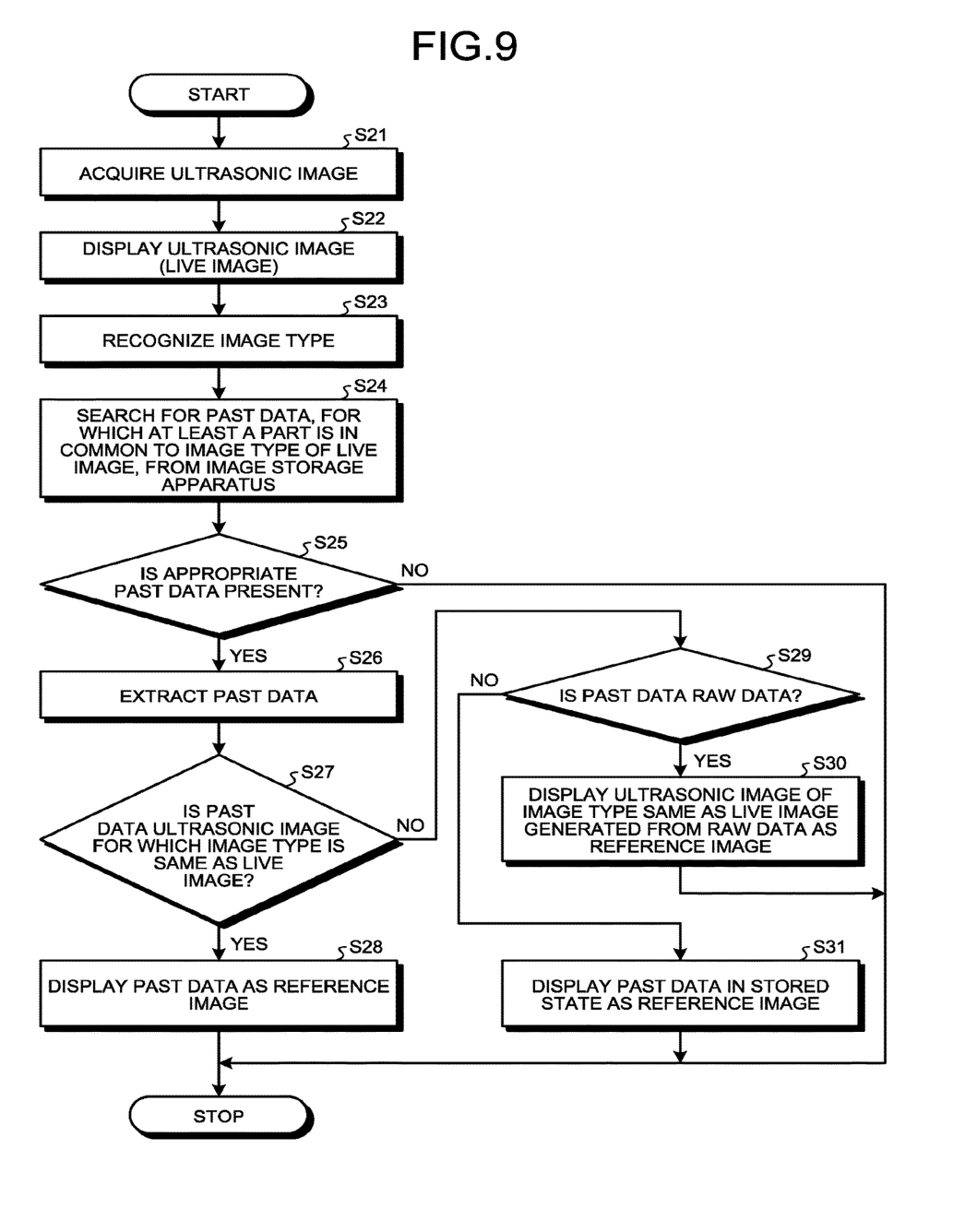
FIG. 9 is a flowchart illustrating one example of a second operation performed by the ultrasonic diagnostic apparatus of the embodiment.

FIG. 9 is a flowchart illustrating one example of the second operation performed by the ultrasonic diagnostic apparatus 100. The second operation is performed when imaging the subject P and the imaging region identical to those of the first operation. Because Step S21 through S23 are the same as those at Step S11 through S13, respectively, of the first operation, the description thereof is omitted.

The extraction function 174 searches, when the image type of the live image is recognized at Step S23, for the past data at least a part of which is in common to the image type, from the image storage apparatus 200 (Step S24). In this case, if there is no appropriate past data (No at Step S25), the second display function 175 terminates the present processing without displaying the reference image.

On the other hand, if there is the past data that satisfies the condition (Yes at Step S25), the extraction function 174 extracts the relevant ultrasonic data from the image storage apparatus 200 (Step S26). Subsequently, the second display function 175 determines whether the extracted past data is the ultrasonic image of the same image type as that of the live image (Step S27). If the extracted past data is the ultrasonic image of the same image type as that of the live image (Yes at Step S27), the second display function 175 displays the extracted past data as the reference image (Step S28) and terminates the present processing.

Furthermore, if the extracted past data is RAW data (No at Step S27→Yes at Step S29), the second display function 175 displays the ultrasonic image of the same image type as that of the live image generated from the RAW data (Step S30) and terminates the present processing.

If the extracted past data is the ultrasonic image for which a part of image types is in common to the live image (No at Step S27→No at Step S29), the second display function 175 displays the extracted ultrasonic data in a stored state as the reference image (Step S31) and terminates the present processing.

When storing the live image collected in the second operation in the image storage apparatus 200, the processing circuitry 170 performs the same processing as that described at Step S14 in the first operation.

As in the foregoing, the ultrasonic diagnostic apparatus 100 in the present embodiment recognizes various image types concerning the live image and displays, together with the live image, the past data at least a part of which is in common to the relevant image types, as the reference image. As a result, the ultrasonic diagnostic apparatus 100 can facilitate the comparison between the live image and the reference image. In addition, because the live image and the reference image can also be displayed in the same display layout, the comparison between the live image and the reference image can be facilitated. As a result, for example, in the observation after stress echo loading or after performing treatment such as puncture ablation or the like, the ultrasonic diagnostic apparatus 100 can achieve improvement in the convenience in displaying the newly obtained live image while referring to the reference image that was obtained before the situation is changed.

The above-described embodiment can also be modified and implemented as appropriate by changing a part of the configurations or functions of the ultrasonic diagnostic apparatus 100. Thus, the following describes some of the modifications concerning the above-described embodiment, as other embodiments. In the following description, the points that are different from those of the above-described embodiment are mainly described, and the details of the points that are in common to the content already described are omitted. The modifications described in the following may be implemented individually, or may be implemented in combination as appropriate.

First Modification

In the above-described embodiment, although it has been described that, when the ultrasonic image for which a part of image types is in common to the image types of the live image is extracted as the past data, the display is made in a stored state as the reference image, the embodiments are not limited thereto.

For example, when a part of the ultrasonic images extracted as the past data represents the image type of the live image, the second display function 175 may display the relevant part of the ultrasonic images as the reference image. For example, when the live image and the past data are the ultrasonic images displayed in the display areas A11 and A12 in FIG. 7, the second display function 175 extracts a portion included in the past data representing the image type identical to the live image, that is, a partial image representing the relevant portion by cutting or enlarging the portion of the superimposed image of the two-dimensional B-mode image and the color Doppler image. Then, the second display function 175 displays the extracted partial image in the display area A12 as the reference image.

As a result, because the live image and the reference image can be made to be the same image type, the comparison between the live image and the reference image can be facilitated, and the same effect as that of the above-described embodiment can be obtained.

Second Modification

In the above-described embodiment, it has been described that, based on the image types of the live image, the reference image at least a part of which is in common to the relevant image types is displayed. However, the display method of the reference image is not limited thereto, and further narrowing conditions or image processing may be applied.

For example, when the brightness of the live image and the reference image differ, the second display function 175 may change the brightness of the reference image to match the live image, and display the reference image after the change. In this case, when the past data corresponding to the reference image is RAW data, the second display function 175 can display, by adjusting the gain of the RAW data, the reference image for which the brightness matches the live image.

As a result, because the reference image and the live image can be viewed in the same way, the convenience in the comparison between the live image and the reference image can be improved.

Third Modification

In the above-described embodiment, it has been described that the past data is extracted from the data stored in the image storage apparatus 200. However, the extraction destination of the past data is not limited to the image storage apparatus 200 and may be the storage 150 and the like of the ultrasonic diagnostic apparatus 100.

Fourth Modification

In the above-described embodiment, it has been described that the mode type, the dimensionality, the layout, and the cross-section type are recognized as the image types of the live image and the ultrasonic image for which a part of the image types is in common is extracted as the past data. However, the condition that the extraction function extracts the past data is not limited to the above-described image types, and the time phase represented in the live image may be used as a further extraction condition.

For example, in the case of ultrasonic diagnosis by using a contrast agent, the image can be divided into three time-phases of an arterial phase, a portal phase, and a late phase depending on the elapsed time from injecting the contrast agent. In this case, the extraction function 174 determines whether the time phase represented in the live image is the arterial phase, the portal phase, or the late phase, and extracts the past data for which the time phase of the same type is represented. Furthermore, for example, when performing ultrasonic diagnosis on the heart, the extraction function 174 extracts the past data that represents the time phase of the type identical to the cardiac phase such as systole, end-diastole, and the like that is represented in the live image.

The extraction function 174 may determine the time phase (cardiac phase and the like) represented in the live image on the basis of the electrocardiogram or the sensing result of a pulse-pressure measurement device and the like. It is assumed that the second display function 175 displays the ultrasonic image based on the past data extracted by the extraction function 174, in synchronization with the time phase represented in the live image.

As a result, because the ultrasonic diagnostic apparatus 100 can display the reference image in which the same type of time phase as that of the live image is represented, the ease of the comparison between the live image and the reference image can be improved. Also, because the ultrasonic diagnostic apparatus 100 can display the live image and the reference image in a state where the time phases are synchronized, the improvement of convenience in comparing both images can be achieved.

Fifth Modification

In the above-described embodiment, it has been described that the ultrasonic image acquired by the acquisition function 171 is displayed as the real-time live image, together with the reference image. However, depending on the environment in which the ultrasonic diagnostic apparatus 100 is used, the usage of displaying only the real-time live image during ultrasonic scanning of the subject P and, after finishing the ultrasonic scanning, displaying the previous live image and the reference image together for confirmation can also be assumed.

Thus, for example, the extraction function 174 and the second display function 175 may, while the ultrasonic scanning is performed by the ultrasonic probe 101, restrain the extraction of the past data and display of the reference image. In this case, the acquisition function 171 also functions as a storage function, and stores the live image data acquired by the ultrasonic scanning in the image memory 140. Furthermore, the acquisition function 171 acquires, after finishing the ultrasonic scanning, the live image data acquired in the previous ultrasonic scanning from the image memory 140 as the ultrasonic image. In addition, the first display function 172 displays on the display 103 the ultrasonic image acquired by the acquisition function 171. Then, the extraction function 174 and the second display function 175 perform the extraction of the past data and display of the reference image, in line with the display of the ultrasonic image by the first display function 172.

As a result, the ultrasonic diagnostic apparatus 100 can display the real-time ultrasonic image (live image) while the ultrasonic scanning of the subject P is performed and, after the ultrasonic scanning is finished, can display the live image acquired by the relevant ultrasonic scanning together with the reference image. Accordingly, because the display of the reference image can be restrained while the ultrasonic scanning is performed, the ultrasonic diagnostic apparatus 100 can cope with a situation where the display of the reference image interferes with the ultrasonic scanning. Furthermore, in checking and the like after the ultrasonic scanning, because the ultrasonic diagnostic apparatus 100 can facilitate the comparison between the ultrasonic image generated in the ultrasonic scanning and the reference image, the improvement of convenience can be achieved.

It may be configured such that the presence or absence of the display of the reference image at the time of ultrasonic scanning is switchable by the operation via the input interface 102, for example. The extraction function 174 and the second display function 175 perform, when the display of the reference image is enabled, the extraction of the past data and the display of the reference image even while the ultrasonic scanning is performed. The extraction function 174 and the second display function 175 restrain, when the display of the reference image is disabled, the extraction of the past data and the display of the reference image while the ultrasonic scanning is performed. Furthermore, for example, when the switching operation is performed while the ultrasonic scanning is performed, the extraction function 174 and the second display function 175 operate according to the setting after switching at the timing at which the switching operation is performed.

In the foregoing embodiments, it has been described that the acquisition unit, the first display unit, the image-type recognition unit, the extraction unit, and the second display unit in the present specification are implemented by the acquisition function 171, the first display function 172, the image-type recognition function 173, the extraction function 174, and the second display function 175 of the processing circuitry 170, but the embodiments are not limited thereto. For example, the same functions may be implemented by hardware-only or in a combination of hardware and software.

The term "processor" used in the foregoing means a central processing unit (CPU), a graphics processing unit (GPU), or the circuitry such as an application-specific integrated circuit (ASIC), a programmable logic device (for example, a simple programmable logic device (SPLD), a complex programmable logic device (CPLD), and a field-programmable gate array (FPGA)), and the like, for example. The processor implements the functions by reading out and executing the programs stored in the storage 150. In place of storing the programs in the storage 150, it does not matter even if the programs are directly incorporated in the circuitry of the processor. In this case, the processor implements the functions by reading out and executing the programs incorporated in the circuitry. The processor in the present embodiment is not limited to be configured as a single circuit and may be configured as a single processor by combining a plurality of independent circuits.

The programs executed by the processor are provided being incorporated in the ROM (read-only memory), storage, and the like in advance. The programs may be recorded and provided in a file of an installable format or an executable format on these devices on a computer-readable storage medium such as a compact disc (CD)-ROM, a flexible disk (FD), a CD-recordable (R), a digital versatile disc (DVD), and the like. Furthermore, the programs may be stored in a computer connected to a network such as the Internet and be provided or distributed by downloading via the network. For example, the programs are configured in modules that include the above-described various function units. As for the actual hardware, as the CPU reads out and executes the programs from the storage medium such as the ROM and the like, each module is loaded on the main storage and is generated on the main storage.

According to at least one of the embodiments in the foregoing, it is possible to display the reference image corresponding to the image type of the live image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
processing circuitry configured to
display, as a live image on a screen, at least one image that represents data output from an ultrasonic probe;
recognize at least one mode type as at least one corresponding image type included in the displayed live image;
extract, from a storage storing a plurality of pieces of data including one or more images collected before the live image, data including an image of the having a same mode type as one of the at least one image included in the live image;
when determining that the live image is a superimposed image made of images having two or more mode types, generate a superimposed image made of other images having the same two or more mode types as the live image from the data extracted from the storage; and
display, as a reference image, the generated superimposed image on the same screen as the live image.

2. The ultrasonic diagnostic apparatus according to claim 1, wherein the processing circuitry is further configured to recognize, as the image type of the live image, dimensionality of the live image.

3. The ultrasonic diagnostic apparatus according to claim 1, wherein the processing circuitry is further configured to recognize, as the image type of the live image, a cross-section type of a cross-section of a subject that the live image represents.

4. The ultrasonic diagnostic apparatus according to claim 1, wherein the processing circuitry is further configured to extract the data including an image of the same mode type as the live image and representing a time phase identical to a time phase that is represented in the live image.

5. The ultrasonic diagnostic apparatus according to claim 1, wherein when an ultrasonic image is extracted out of the one or more images collected before the live image, the processing circuitry is further configured to display, as the reference image, the extracted ultrasonic image on the same screen as the live image.

6. The ultrasonic diagnostic apparatus according to claim 1, wherein when raw data for generating an ultrasonic image of the same mode type as the live image is extracted out of the one or more images collected before the live image, the processing circuitry is further configured to display, as the reference image, the ultrasonic image based, on the raw data, on the same screen as the live image.

7. The ultrasonic diagnostic apparatus according to claim 1, wherein, in the recognizing, the processing circuitry is further configured to recognize any of a B mode, an M mode, a color Doppler mode, and a pulse Doppler mode as the mode type of the live image.

8. An ultrasonic diagnostic apparatus, comprising:
processing circuitry configured to display, as a live image on a screen, at least one image that represents data output from an ultrasonic probe;

store the live image in a memory;

recognize at least one mode type as at least one corresponding image type included in the displayed live image;

extract, from a storage storing a plurality of pieces of data including one or more images collected before the live image, data including an image of the having a same mode type as one of the at least one image included in the live image;

when determining that the live image is a superimposed image made of images having two or more mode types, generate a superimposed image made of other images having the same two or more mode types as the live image from the data extracted from the storage; and display, as a reference image, the generated superimposed image on the same screen as the live image, in line with a display of the live image stored in the memory.

9. An ultrasonic diagnostic method, comprising:

displaying, as a live image on a screen, at least one image that data output from an ultrasonic probe represents;

recognizing at least one mode type as at least one corresponding image type included in the displayed live image;

extracting, from a storage storing a plurality of pieces of data including one or more images collected before the live image, data including an image of the having a same mode type as one of the at least one image included in the live image;

determining that the live image is a superimposed image made of images having two or more mode types, and generating a superimposed image made of other images having the same two or more mode types as the live image from the data extracted from the storage; and displaying, as a reference image, the generated superimposed image on the same screen as the live image.

10. An ultrasonic diagnostic method, comprising:

displaying, as a live image on a screen, at least one image that represents data output from an ultrasonic probe;

storing the live image in a memory;

recognizing at least one mode type as at least one corresponding image type included in the displayed live image;

extracting, from a storage storing a plurality of pieces of data including one or more images collected before the live image, data including an image of the having a same mode type as one of the at least one image included in the live image;

determining that the live image is a superimposed image made of images having two or more mode types, and generating a superimposed image made of other images having the same two or more mode types as the live image from the data extracted from the storage; and displaying, as a reference image, the generated superimposed image on the same screen as the live image, in line with a display of the live image stored in the memory.

* * * * *